United States Patent [19]

Masilamani et al.

[11] Patent Number: 4,510,321
[45] Date of Patent: Apr. 9, 1985

[54] AUTOXIDATIVE CLEAVAGE OF KETONES IN THE PRESENCE OF PULVERIZED ALKALI METAL HYDROXIDE

[75] Inventors: Divakaran Masilamani, Morristown; Edward H. Manahan, Morris Plains, both of N.J.

[73] Assignee: Allied Corporation, Morris Township, Morris County, N.J.

[21] Appl. No.: 462,295

[22] Filed: Jan. 31, 1983

[51] Int. Cl.$^3$ .................. C07C 27/00; C07C 45/33; C07C 51/245; C07C 51/255
[52] U.S. Cl. .................. 562/421; 260/396 R; 260/413; 562/500; 562/504; 562/505; 562/506; 562/508; 562/509; 562/511; 562/527; 562/528; 562/530; 568/312; 568/344; 568/386
[58] Field of Search ............. 562/400, 421, 500, 504, 562/505, 506, 509, 511, 508, 528, 530, 527; 568/312, 386, 344; 260/396 R, 413 M, 413 Q

[56] References Cited

U.S. PATENT DOCUMENTS

| 2,005,183 | 6/1935 | Flemming et al. | 562/527 |
| 2,241,487 | 5/1941 | Slotterbeck | 562/400 |
| 3,356,722 | 12/1967 | Wallace et al. | 562/504 |
| 3,419,605 | 12/1968 | Mead | 562/421 |
| 3,933,903 | 1/1976 | Havinga et al. | 562/504 |
| 4,018,827 | 4/1977 | Rao et al. | 260/586 P |

OTHER PUBLICATIONS

J. Organic Chemistry, vol. 30, (1965), pp. 3768-3771; Wallace et al.
J. Organic Chemistry, vol. 42, (1977), pp. 3754-3755; K. Yang et al.
W. V. E. Doering et al., (J. Am. Chem. Soc., 1954, 76, 482-486), Alkoxide-Catalyzed Autoxidative Cleavage of Ketones and Esters.
H. R. Gersmann et al., (J. Chem. Soc. B, 1971, 2230-2237), Autoxidation of Ketones and Esters in Basic Solution.
R. C. P. Cubbon et al., (J. Chem. Soc. C., 1968, 2978-2982), Organic Peroxides Containing Functional Groups. Part 1. The Preparation and Properties of Some α-Oxo-hydroperoxides.
D. V. Rao et al., (J. Org. Chem., 1979, vol. 44, 456-458, Base-Catalyzed Autoxidation of Cyclic Ketones.
Novel Carbon Catalysis: Oxidation in Basic Solution.
Solvent Effects in the Base-Catalyzed Oxidation of Ketones to Mono- and Dicarboxylic Acids.
A. Robertson et al., (J. Chem. Soc., 1948, Pt. 2, 1574-1578), Studies of the Autoxidation of Tetralin. Part 1. Investigation of Autoxidation Products.

Primary Examiner—Natalie Trousof
Assistant Examiner—Patricia M. Scott
Attorney, Agent, or Firm—Thomas D. Hoffman; Gerhard H. Fuchs

[57] ABSTRACT

Processes for the autoxidative cleavage of selected ketones such as $C_4$–$C_{10}$ cycloalkanones having at least one hydrogen or at least one R group on a carbon alpha to the carbonyl carbon or aryl alkyl ketones having the formula III

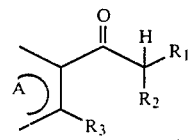

comprising contacting a liquid phase comprising said ketone with elemental oxygen gas, preferably air, in the presence of a pulverized alkali metal hydroxide at a temperature of no more than 50° C. for a time sufficient to produce an oxidized product are disclosed. Preferred cycloalkanones, 2-alkyl- and 2-arylcyclohexanone are autoxidized in pulverized sodium hydroxide/dimethoxyethane to produce 6-alkyl- or 6-aryl-6-oxohexanoic acids, respectively.

18 Claims, No Drawings

AUTOXIDATIVE CLEAVAGE OF KETONES IN THE PRESENCE OF PULVERIZED ALKALI METAL HYDROXIDE

BACKGROUND OF THE INVENTION

This invention relates to the autoxidative cleavage of selected ketones having at least one hydrogen on carbon alpha to the carbonyl carbon, such as $C_4$–$C_{10}$ cycloalkanones and aryl alkyl ketones, comprising contacting a liquid phase comprising said ketone with elemental oxygen gas in the presence of a pulverized alkali metal hydroxide at a temperature of no more than about 50° C. for a time sufficient to produce an oxidized product.

Autoxidations of organic compounds such as hydrocarbons and ketones use molecular oxygen and are catalyzed by base. Base-catalyzed autoxidations usually employ strong bases such as alkali metal amides, hydrides or alkoxides and are known to effect cleavage of the carbon-carbon and carbon-hydrogen bonds alpha to the carbonyl carbon. For example, cyclohexanone, in the presence of base, is autoxidized into alpha-hydroperoxycyclohexanone and cyclohexane-1,2-dione (products of carbon-hydrogen bond cleavage) and condensation products of the ketone starting material and diketone product or is autoxidized into reaction mixtures containing adipic acid, lower diacids (products of carbon-carbon bond cleavage) and product(s) of carbon-hydrogen bond cleavage and mixtures of condensation products including condensation products of carbon-carbon cleavage products and of the ketone starting material.

Prior art base-catalyzed autoxidations are homogeneous, produce complicated product mixtures, consume at least stoichiometric quantities of strong base, operate under anhydrous as well as homogeneous conditions with aprotic solvents such as hexamethylphosphoramide and molecular oxygen gas and usually at temperatures below 0° C. Accordingly prior art base-catalyzed autoxidations produce complicated product mixtures, poor selectivities and as such are economically unattractive for commercial scale operation.

SUMMARY OF THE INVENTION

The present invention provides a process for autoxidation of a $C_4$–$C_{10}$ cycloalkanone having at least one hydrogen on a carbon alpha to the carbonyl carbon which comprises contacting a liquid phase comprising said $C_4$–$C_{10}$ cycloalkanone with elemental oxygen gas in the presence of a pulverized alkali metal hydroxide at a temperature of no more than about 50° C. for a time sufficient to cleave the bond between the alpha carbon and the carbonyl carbon.

The present invention also provides a process for the autoxidation of a $C_4$–$C_{10}$ cycloalkanone having at least one R group on the carbon alpha to the carbonyl carbon to a keto-alkanoic acid which comprises contacting a liquid phase comprising said $C_4$–$C_{10}$ cycloalkanone with an elemental oxygen gas in the presence of a pulverized alkali metal hydroxide at a temperature of no more than about 50° C. for a time sufficient to produce a keto-alkanoic acid.

The present invention further provides a process for the autoxidation of an aryl alkyl ketone having the formula III:

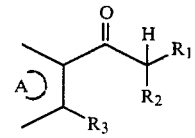

wherein A is part of an aromatic ring system, wherein $R_1$, $R_2$, and $R_3$ are independently hydrogen, $C_1$–$C_{10}$ alkyl, $C_4$–$C_{10}$ cycloalkyl or aryl or wherein $R_3$ forms part of a fused alicyclic ring with $R_2$ or $R_1$, which comprises contacting a liquid phase comprising said aryl alkyl ketone with an elemental oxygen gas in the presence of a pulverized alkali metal hydroxide at a temperature of no more than about 50° C. for a time sufficient to produce an oxidized product.

DETAILED DESCRIPTION OF THE INVENTION

The autoxidations of the present invention are carried out by contacting powdered alkali metal hydroxide with a solution of the ketone in organic solvents such as a $C_1$–$C_8$ alcohol or aprotic solvent usually dimethoxyethane at a temperature of no more than about 50° C. The reaction temperature may be as low as −10° C. to 50° C. but preferably is from about 20° C. to about 50° C., more preferably 20° C.–25° C. The reaction mixture so formed is flushed with elemental oxygen gas and stirred under oxygen for a time sufficient to produce the desired autoxidation product. The order in which the reactants are brought together is not critical. The alkali metal hydroxides, preferably sodium hydroxide or potassium hydroxide, are commercially available materials that usually contain about 15 weight % water and are simply pulverized without further purification or drying. In a preferred embodiment of the autoxidation process of the present invention, the organic solvent is an aprotic solvent, especially dimethoxyethane or is a $C_3$–$C_8$ alcohol, the alkali metal hydroxide is sodium hydroxide, air is used as the source of elemental oxygen gas, and the reaction mixture maintained at room temperature is non-homogeneous.

The autoxidized products (see Tables A & B hereinbelow), as the sodium salt(s), for example the disodium salt of adipic acid (13) from cyclohexanone (6), the sodium salt of 6-methyl-6-oxohexanoic acid (8) from 2-methylcyclohexanone (1) or the sodium salt of 2-hydroxy-1,4-naphthaquinone (32) from 1-tetralone (18), are precipitated under the heterogeneous reaction conditions and further oxidation is thus prevented. The work-up procedure involves a simple filtration and acidification; the reaction solvent, a $C_3$–$C_8$ alcohol or dimethoxyethane containing unreacted ketone is recovered and recycled to the process of the present invention without purification such as by distillation.

The reaction is conducted in any appropriate closed vessel in which an oxygen atmosphere can be maintained. Advantageously oxygen gas is bubbled into the mixture of base and organic solvent prior to and throughout the addition of the ketone to the mixture. The base is advantageously employed in an amount corresponding to about 1.0 moles to about 2.0 moles per mole of ketone and preferably in an amount corresponding to about 1.0 moles to about 2.0 moles per mole of ketone. The amount of solvent employed is not critical and can vary over a wide range depending upon the relative solubility of the base in said solvent. The amount of solvent employed is generally dictated by economic considerations, particularly where the process of the invention is to be carried out on a commercial scale.

The autoxidation generally proceeds rapidly and its progress can be followed by uptake of oxygen gas and by routine analytical procedures, such as infrared spectroscopy, nuclear magnetic resonance spectroscopy, and the like, carried out on aliquots of the reaction mixture.

The organic solvents employed to dissolve the ketones autoxidized in accordance with the process of the present invention are advantageously $C_1$–$C_8$ alcohols, aprotic ethers such as dialkyl ethers, dialkyl ethers of polyalkylene glycols, tetrahydrofuran, dioxane and the like that remain liquid at the reaction temperatures employed. The $C_1$–$C_8$ alcohols found useful in the process of the present invention are methanol, ethanol, propanol, butanol, pentanol, hexanol, heptanol, octanol and isomeric analogues thereof. The dialkyl ethers found useful in the process of the present invention have alkyl groups consisting of 1–8 carbons and contain up to 16 carbon atoms. The preferred dialkyl ethers include diethyl ether, di n-propyl ether and di n-butyl ether. The dialkyl ethers of polyalkylene glycol have alkyl groups consisting of 1–6 carbon atoms, alkylene groups consisting of 2 or 3 carbon atoms and contain from 4 to 20 carbon atoms. The preferred dialkyl ethers of polyalkylene glycols have 1 to 3 carbon atoms in each alkyl group and 2 or 3 ethylene groups. Typical examples of suitable dialkyl ethers of polyalkylene glycols include dimethoxyethane, diglyme [$CH_3O(C_2H_4O)_2CH_3$], triglyme [$CH_3O(C_2H_4O)_3CH_3$] and tetraglyme [$CH_3O(C_2H_4O)_4CH_3$].

The preferred organic solvents are aprotic ethers. The most preferred aprotic ether is dimethoxyethane. It is a special feature of the process of the present invention that no special precautions such as drying or purification of the organic solvents, most preferably dimethoxyethane, are required for use of organic solvents. In a preferred embodiment of the process of the present invention, 2-alkyl and 2-aryl cyclohexanones are autoxidized under nonhomogeneous conditions using sodium hydroxide in aprotic ethers, preferably dimethoxyethane or in $C_3$–$C_8$ alcohols. It is another special feature of the preferred embodiment of the present invention that the aprotic ether or $C_3$–$C_8$ alcohol solvents are recovered from the non-homogeneous autoxidation reaction mixture of the present invention by filtration or decantation and may be recycled to the process of the present invention without distillation or drying.

Among the useful $C_4$–$C_{10}$ cycloalkanones having at least one hydrogen on a carbon alpha to the carbonyl carbon are $C_4$–$C_{10}$ cycloalkanones having the formulas I and Ia

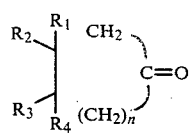

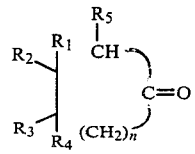

wherein n=0 to 6 and wherein $R_1$, $R_2$, $R_3$, $R_4$ and $R_5$ are independently hydrogen, $C_1$–$C_{10}$ alkyl, aryl and $C_4$–$C_{10}$ cycloalkyl or wherein $R_1$ or $R_2$ forms a fused alicyclic ring with $R_3$ or $R_4$ or wherein $R_1$, $R_2$, $R_3$ and $R_4$ form an aromatic ring. Particularly useful are $C_4$–$C_{10}$, preferably $C_5$–$C_7$ cycloalkanones wherein $R_1$–$R_4$ are hydrogen or wherein at least one of the $R_{1-4}$ groups is $C_1$–$C_{10}$ alkyl, preferably $C_1$–$C_6$ alkyl or $C_4$–$C_{10}$ cycloalkyl, preferably $C_5$–$C_7$ cycloalkyl or aryl, preferably phenyl, benzyl or $C_1$–$C_3$ alkyl aryl or wherein $R_1$ or $R_2$ forms a $C_5$–$C_7$ fused alicyclic ring, preferably $C_5$–$C_6$ fused alicyclic ring with $R_3$ or $R_4$ and $R_1$ or $R_2$ which is not part of fused alicyclic ring is hydrogen or $C_1$–$C_6$ alkyl or wherein $R_1$, $R_2$, $R_3$ and $R_4$ forms an aromatic ring, preferably a benzene ring. Preferred cycloalkanones are cyclopentanone, cyclohexanone, cycloheptanone, 3- and 4-($C_1$–$C_{10}$)-alkyl cyclopentanone, 3- and 4-($C_1$–$C_{10}$)-alkylcyclohexanone, 3- and 4-phenylcyclopentanone, 3- and 4-phenylcyclohexanone, bicyclo[4.3.0]-nonan-2-one, 2-tetralone, and 1-substituted-2-tetralones such as 1-($C_1$–$C_{10}$)alkyl-, 1-($C_4$–$C_{10}$cycloalkyl) and 1-aryl-2-tetralones.

Among the useful $C_4$–$C_{10}$ cycloalkanones having at least one R group which may be $C_1$–$C_{10}$ alkyl, $C_4$–$C_{10}$ cycloalkyl or aryl on a carbon alpha to the carbonyl carbon are $C_4$–$C_{10}$ cycloalkanones having the formulas II, IIa and IIb

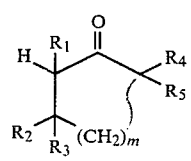

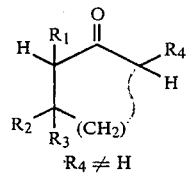

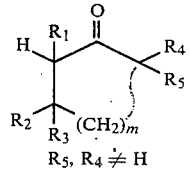

wherein m=0–6 and wherein $R_1$, $R_2$ and $R_3$ are independently $C_1$–$C_{10}$ alkyl, $C_4$–$C_{10}$ cycloalkyl or aryl or wherein $R_2$ and $R_3$ are hydrogen and $R_1$ is defined as hereinabove or wherein $R_1$ forms a fused alicyclic ring with $R_2$, and $R_3$ is defined as hereinabove, and wherein $R_4$ and $R_5$ are independently hydrogen, $C_1$–$C_{10}$ cycloalkyl, $C_1$–$C_{10}$ alkyl or aryl. Among the $C_4$–$C_{10}$ cycloalkanones particularly useful in the autoxidation of the present invention are 2-substituted $C_4$–$C_{10}$ cycloalkanones especially 2-($C_1$–$C_{10}$ alkyl)cyclopentanone, 2-arylcyclopentanone, 2-($C_4$-$C_{10}$ cycloalkyl)cyclopentanone and 2-($C_1$-$C_{10}$ alkyl)cyclohexanone, 2-arylcyclohexanone and 2-($C_4$-$C_{10}$ cycloalkyl)cyclohexanone.

Among the useful aryl alkyl ketones are those ketones having the formulas III, IV and V

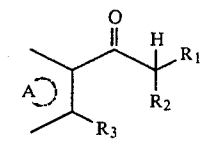  III

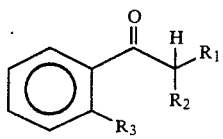  IV

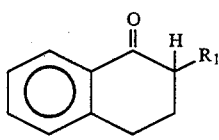  V wherein A is part of an aromatic ring system, wherein $R_1$, $R_2$, and $R_3$ are independently hydrogen, $C_1$-$C_{10}$ alkyl, $C_4$-$C_{10}$ cycloalkyl or aryl or wherein $R_3$ forms part of a fused alicyclic ring with $R_2$ or $R_1$. Pariculary useful aryl alkyl ketones for the autoxidation of the present invention are ketones wherein A forms a benzene ring as in formulas IV and V or wherein $R_{1\text{-}3}$ are hydrogen or wherein $R_{1\text{-}3}$ are $C_1$-$C_6$ alkyl or $C_4$-$C_{10}$ cycloalkyl, preferably $C_5$-$C_7$ cycloalkyl or aryl, preferably phenyl, benzyl or alkylaryl or wherein $R_3$ and $R_2$ form a $C_5$-$C_7$ fused alicyclic ring and $R_1$ is hydrogen or $C_1$-$C_6$ alkyl.

For $R_1$-$R_5$ in formulas I, Ia IIa-c, III, IV and V the suitable $C_1$-$C_6$ alkyl radicals include methyl, ethyl, propyl, isopropyl, n-butyl, iso-butyl, sec-butyl, t-butyl, n-pentyl, n-hexyl, sec-hexyl, iso-hexyl; the suitable $C_4$-$C_{10}$ cycloalkyl radicals include, cyclobutyl, cyclopentyl, methylcyclopentyl, cyclohexyl, methylcyclohexyl, cycloheptyl, cyclooctyl, cyclononyl, and cyclodecyl. One or more inert substituents which do not interfere with the autoxidation process of the present invention may also be present in the formulas I-V and may even be $R_1$-$R_5$. Illustrative of inert substituents useful in the process of the present invention are $C_1$-$C_6$ alkoxy such as methoxy, ethoxy, propoxy, butoxy, pentoxy, hexyloxy and isomeric forms thereof.

The autoxidation products of $C_4$-$C_{10}$ cycloalkanones having only hydrogen on carbons alpha to the carbonyl carbon are dicarboxylic acids.

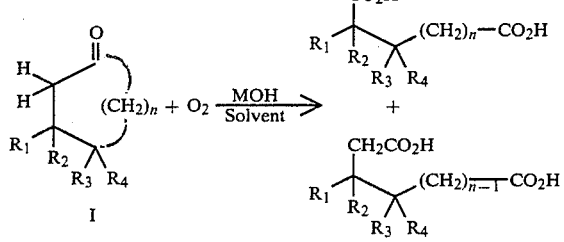

I

The autoxidation products of the $C_4$-$C_{10}$ cycloalkanones having at least one R group on the carbon alpha to the carbonyl carbon and having formulas II, IIa, IIb and IIc are ketoalkanoic acids.

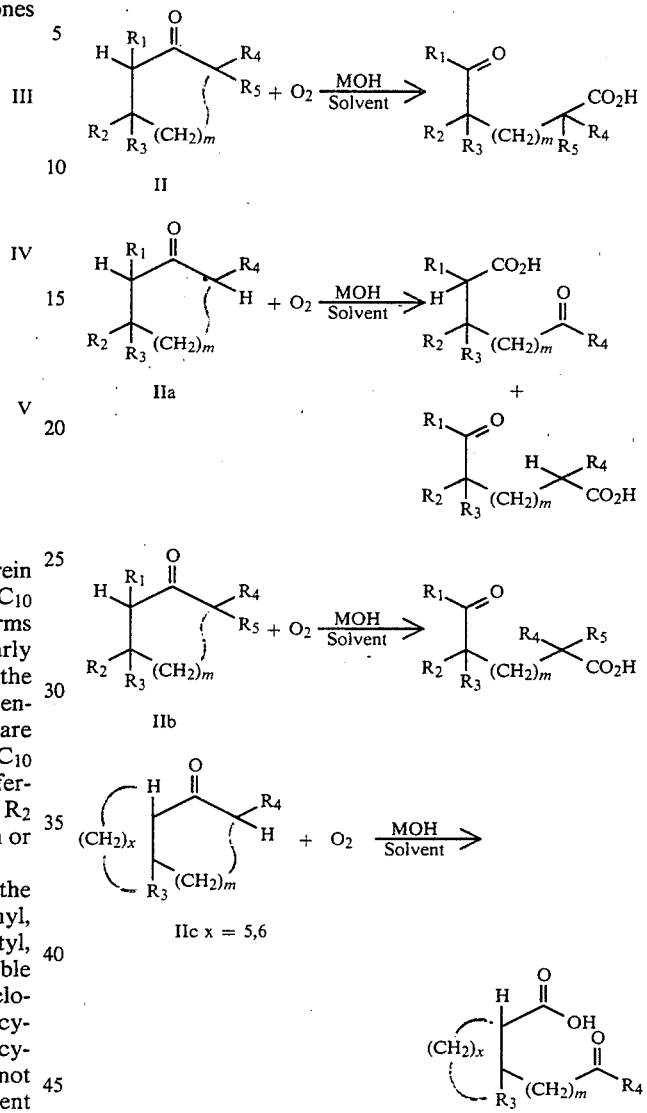

The autoxidation products of aryl alkyl ketones having the formulas III and IV are benzoic acids and alkanoic acid or ketones.

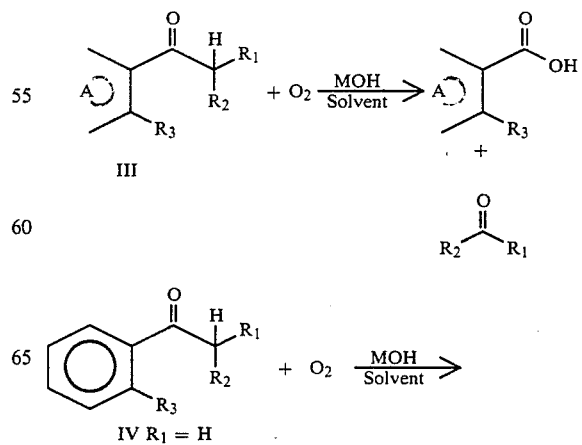

IV $R_1$ = H

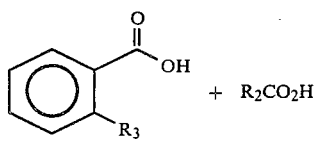

When $R_1=R_3=H$ and $R_2=C_6H_5-$ are substituents in IV, the autoxidation products observed were benzoic acid and benzil.

The autoxidation products of alkyl aryl ketones having formulas V and Va are products of C-H cleavage

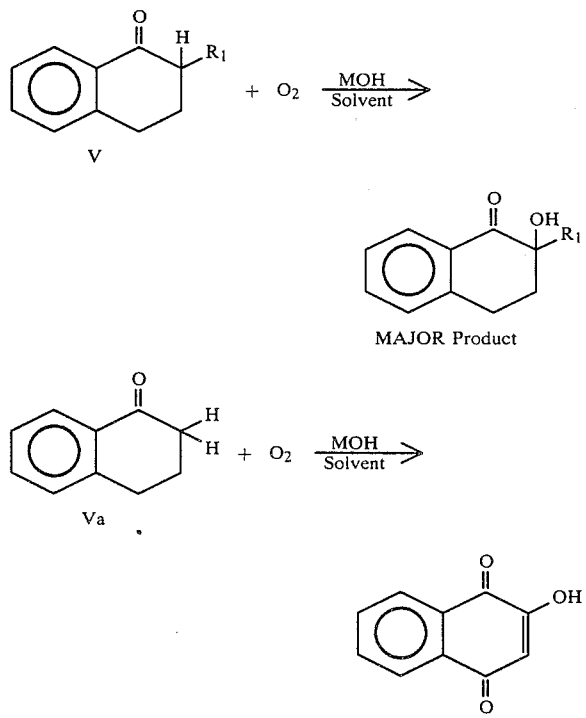

The reaction may be run under atmospheric pressure, subatmospheric pressure or superatmospheric pressure of oxygen. The contact times vary from 1 hour to 22 hours with the structure of the starting ketone. See Tables A and B hereinbelow.

EXPERIMENTAL SECTION

Melting points are uncorrected. The $^1$H NMR and IR spectra were recorded on Varian T-60 and Perkin-Elmer 128 spectrometers, respectively.

Sodium hydroxide (MCB) was used without purification and 1,2-dimethoxyethane (DME) supplied by Baker was used without distillation. 2-Cyclohexylcyclohexanone was supplied by Fluka and methylcyclohexylketone was supplied by Chemical Sampling Company. All the other ketones were obtained from Aldrich Chemical Company. The ketones were used without further purification.

EXAMPLE 1

Autoxidation of Ketones Over Solid Sodium Hydroxide

General Procedure: Sodium hydroxide (0.01 or 0.02 mol) was powdered and added to a flask (100 mL) containing a solution of 0.01 mol of a ketone in 50 mL of dimethoxyethane (DME). The flask was flushed with oxygen and the heterogeneous mixture was stirred under oxygen. A gas burette was used to measure the uptake of oxygen. After the reaction had stopped, the product was filtered using a sinter funnel. The filtrate contained the unreacted ketone. The precipitate was neutralized with a 1 Molar HCl (to pH 2) and extracted with ether. The ether extract was dried ($Na_2SO_4$) and concentrated to yield the acidic product. The acids were purified by crystallization or distillation. In some cases, they were converted to the methylester and then distilled to obtain the pure ester. The results are summarized in Tables A and B. The products listed in Tables A and B were only products formed. Thus, selectivities for autoxidations of the present invention were almost 100%

The products were identified by $^1$H NMR and IR spectral analysis and by comparison of physical properties with literature values.

In the autoxidation of deoxybenzoin (17) and 2-methyl-1-tetralone (19), the filtrate contained benzil (23) and 2-hydroxy-2-methyl-1-tetralone (36), respectively.

It is also convenient to carry on the autoxidation in a 100-mL Fisher bottle. Oxygen was pressurized to 50 psig. The oxidation was faster (by roughly 20%). However, the oxygen uptake was only roughly estimated from the drop in pressure.

When air was used instead of oxygen, it was bubbled through the reaction mixture at the rate of 50–100 mL/min. The progress of the reaction was followed by glc analysis of the unreacted ketone using a suitable internal standard.

TABLE A

Autoxidation[a] of Cyclohexanones and Methylcyclohexyl Ketone over Solid Sodium Hydroxide

| Ketone | Ratio NaOH/Ketone | Time Hrs. | Product (Yield)[b] |
|---|---|---|---|
| 1 (methylcyclohexyl ketone) | 1.0 | 18 | 8 (95%)[c] (cyclohexane-CO$_2$H) |
| 2 (cyclohexyl cyclohexyl ketone) | 1.0 | 22 | 9 (55%)[c] |
| 3 (cyclohexyl phenyl ketone) | 1.0 | 1.5 | 10 (93%)[c] |
| 4 (1-methyl-2-tetralone type) | 1.0 | 3.0 | 11 (46%)[c] |
| 5 (2-tetralone) | 2.0 | 18 | 12 (63%)[d] |

TABLE A-continued
Autoxidation[a] of Cyclohexanones and Methylcyclohexyl Ketone over Solid Sodium Hydroxide

| Ketone | Ratio NaOH/Ketone | Time Hrs. | Product (Yield)[b] |
|---|---|---|---|
|  cyclohexanone | 2.0[c] | 18 | 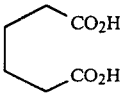 13 (30%)[d,e,f] |
|  methyl cyclohexyl ketone | 1.0 | 18 | No Reaction |

FOOTNOTES TO TABLE A
[a] 0.01 Mol of ketone dissolved in 50 mL of DME was reacted with oxygen at room temperature.
[b] Isolated crude yield (based on ketone) of only product formed; the rest was unreacted ketone. Thus, selectivity for each autoxidation was almost 100%.
[c] 6-substituted-6-oxyhexanoic acids were only product formed. 2-substituted adipic acids expected from $C_1-C_6$ bond cleavage of 1 and 1,2-cyclohexanediones expected from $C_6-H$ bond cleavage were not observed even in trace amounts.
[d] Adipic acid or substituted adipic acid was only product formed.
[e] When 1 g of activated charcoal was added, the yield was increased to 60%.
[f] Adipic Acid (as its disodium salt) was the only product formed. 1,2-cyclohexanedione and aldol condensation products were not formed even in trace amounts.

TABLE B
Autoxidation[a] of Aromatic Ketones over Solid Sodium Hydroxide

| Ketone | Ratio NaOH/Ketone | Time Hrs. | Products (Yield)[b] | |
|---|---|---|---|---|
| 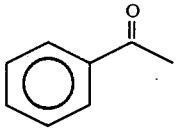 14 | 2.0[c] | 18 | 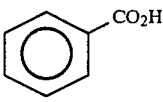 20 (25%)[d] | |
| 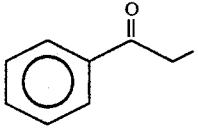 15 | 2.0[c] | 18 | 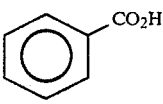 20 (63%) | $CH_3CO_2H$ 21 (63%) |
|  16 | 1.0[c] | 18 | 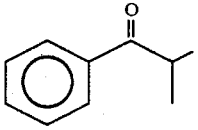 20 (63%) | 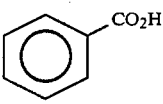 $CH_3CCH_3$ 22 (73%) |
|  17 | 2.0[c] | 18 | 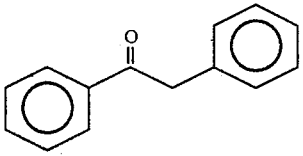 20 (60%)[d] | 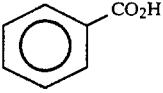 23 (62%) |
| 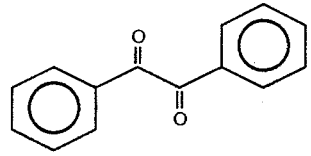 18 | 2.0 | 18 | 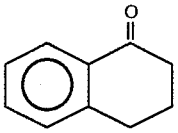 32 (50%) | |
| 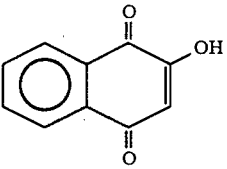 19 | 1.0 | 1.0 | 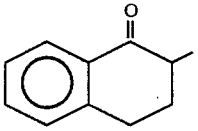 36 (70%) | 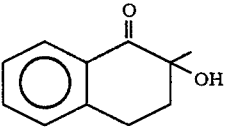 38 (10%) |

TABLE B-continued

Autoxidation[a] of Aromatic Ketones over Solid Sodium Hydroxide

| Ketone | Ratio NaOH/Ketone | Time Hrs. | Products (Yield)[b] |
|---|---|---|---|
| | | | 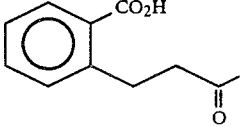<br>37 (20%) |

FOOTNOTES TO TABLE B

[a] 0.01 Mol of ketone dissolved in 50 mL of DME was reacted with oxygen at room temperature. The autoxidations of ketones 14 and 15, which contain primary and secondary hydrogens, respectively, alpha to carbonyl were very slow in the absence of added activated charcoal even though same yields of same products were obtained. However, the autoxidations of ketones 16 and 17, which contain tertiary and benzylic hydrogens alpha to the carbonyl, respectively, produced the same yields of products in the absence of added activated charcoal after only about 27 hrs.

[b] Isolated crude yield based on ketone. (The rest is unreacted ketone).

[c] 1 g of activated charcoal was used.

[d] Yield of benzoic acid was 5–10% after 18 hours in absence of added charcoal. Formic acid, though not observed, was presumably formed and oxidized to $CO_2$ and $H_2O$.

[e] Corresponds to 30% conversion of 17.

EXAMPLE 2

The autoxidation of cyclohexanone (0.98 g, 0.01 mol) in 50 mL of ethanol containing sodium hydroxide (0.8 g, 0.02 mol) proceeded smoothly at room temperature in the apparatus of Example 1. About 90% of the cyclohexanone was converted in five hours and two mole equivalent of oxygen was taken up. Since each molecule of cyclohexanone needs only 1.5 equivalent of oxygen for its conversion to adipic acid, the uptake of excess oxygen was an indication that the oxidation has proceeded beyond adipic acid formation. The analysis of the reaction product (by gc-mass spectrometer) showed adipic acid and its monoethyl ester to an extent of 60%. The remainder was made up of glutaric acid, succinic acid, and their ethyl ethers, as well as a number of aldol condensation products. Addition of activated charcoal (1 g) accelerated the autoxidation, but the products were essentially the same.

EXAMPLE 3

The procedure of Example 2 was followed excepting that the reaction mixture was heated to reflux. The solubility of oxygen in the ethanolic sodium hydroxide was too low for the autoxidation to be effective and only aldol condensation products of cyclohexanone were observed.

We claim:

1. A process for autoxidation of a $C_4$–$C_{10}$ cycloalkanone having at least one hydrogen on a carbon alpha to the carbonyl carbon which comprises contacting, under nonhomogeneous conditions, a liquid phase comprising said $C_4$–$C_{10}$ cycloalkanone and an aprotic ether with elemental oxygen gas in the presence of a pulverized alkali metal hydroxide at a temperature of no more than about 50° C. for a time sufficient to cleave the bond between the alpha carbon and the carbonyl carbon to produce a reaction mixture of an insoluble alkali metal salt of an oxidized product, substantially free of further oxidation products, the alkali metal salt of the oxidized product being selected from an alkali metal salt of a keto-alkanoic acid, a dialkali metal salt of a dicarboxylic acid, or an alkali metal salt of a benzoate and a liquid phase comprising the the aprotic ether and said $C_4$–$C_{10}$ cycloalkanone, separating the reaction mixture into the insoluble alkali metal salt of the oxidized product and said liquid phase, and recovering the alkali metal salt of the oxidized product.

2. The process of claim 1 wherein the temperature is in the range of about −10° C. to 50° C.

3. The process of claim 1 wherein the cycloalkanone has the formula I:

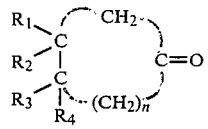

wherein n=0 to 6 and wherein $R_1$, $R_2$, $R_3$ and $R_4$ are independently hydrogen, $C_1$–$C_{10}$ alkyl, aryl, and $C_4$–$C_{10}$ cycloalkyl or wherein $R_1$ or $R_2$ forms a fused alicyclic ring with $R_3$ or $R_4$ or wherein $R_1$, $R_2$, $R_3$, and $R_4$ form an aromatic ring and wherein the autoxidation product is a dicarboxylic acid.

4. The process of claim 3 wherein the aprotic ether is dimethoxyethane and wherein the alkali metal hydroxide is sodium hydroxide.

5. The process of claim 4 wherein the reaction mixture comprises an insoluble disodium salt of a dicarboxylic acid, substantially free of further oxidation products, and a liquid phase comprising dimethoxyethane and said $C_4$–$C_{10}$ cycloalkanone, and wherein the reaction mixture is separated into the disodium salt of a dicarboxylic acid and the liquid phase comprising dimethoxyethane and said $C_4$–$C_{10}$ cycloalkanone, and wherein the dicarboxylic acid is recovered and the liquid phase is recycled for contacting with additional $C_4$–$C_{10}$ cycloalkanone and elemental oxygen gas.

6. A process for the autoxidation of a $C_4$–$C_{10}$ cycloalkanone having at least one R group selected from a group consisting of $C_1$–$C_{10}$ alkyl, $C_4$–$C_{10}$ cycloalkyl and aryl, on the carbon alpha to the carbonyl carbon to a keto-alkanoic acid which comprises contacting, under nonhomogeneous conditions, a liquid phase comprising said $C_4$–$C_{10}$ cycloalkanone and an aprotic ether with an elemental oxygen gas in the presence of a pulverized alkali metal hydroxide at a temperature of no more than about 50° C. for a time sufficient to produce a reaction mixture comprising of an insoluble alkali metal salt of a keto-alkanoic acid, substantially free of further oxidation products, and a liquid phase comprising the aprotic ether, separating the reaction mixture onto the insoluble alkali metal salt of the keto-alkanoic acid and said liquid phase and recovering the alkali metal salt of the keto-alkanoic acid.

7. The process of claim 6 wherein said $C_5$–$C_{10}$ cycloalkanone has the formula II:

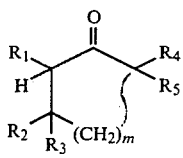  II wherein m is 1 to 6 and wherein $R_1$, $R_2$, and $R_3$ are independently $C_1$–$C_{10}$ alkyl, $C_4$–$C_{10}$ cycloalkyl, aryl or wherein $R_2$ and $R_3$ are hydrogen and $R_1$ is defined as herein above or wherein $R_1$ forms a fused alicyclic ring with $R_2$ or $R_3$ and wherein $R_4$ and $R_5$ are independently hydrogen, $C_1$–$C_{10}$ cycloalkyl, $C_1$–$C_{10}$ alkyl or aryl.

8. The process of claim 6 wherein said cycloalkanone is selected form the group consisting of 2-($C_1$–$C_{10}$)alkylcyclohexanone, 2-arylcyclohexanone and 1-($C_1$–$C_{10}$)alkyl-2-tetralone.

9. The process of claim 6 wherein the aprotic ether is dimethoxyethane.

10. The process of claim 6 wherein the alkali metal hydroxide is sodium hydroxide.

11. A process for the autoxidation of an aryl alkyl ketone having the formula III:

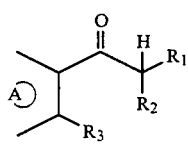

wherein A is part of an aromatic ring system, wherein $R_1$, $R_2$, and $R_3$ are independently hydrogen, $C_1$–$C_{10}$ alkyl, $C_4$–$C_{10}$ cycloalkyl or aryl or wherein $R_3$ formed part of a fused alicyclic ring with $R_2$ or $R_1$, which comprises contacting, under non-homogeneous conditions, a liquid phase comprising said aryl alkyl ketone and a $C_3$–$C_8$ alcohol or an aprotic ether with an elemental oxygen gas in the presence of a pulverized alkali metal hydroxide at a temperature of no more than about 50° C. for a time sufficient to produce a reaction mixture comprising an insoluble alkali metal salt of an oxidized product, being an alkali metal salt of a keto-alkanoic acid, of a dicarboxylic acid or of a benzoate, and a liquid phase comprising the $C_3$–$C_8$ alcohol or the aprotic ether, the reaction mixture being substantially free of further oxidation products, separating the reaction mixture into the insoluble alkali metal salt of the oxidized product and the liquid phase and recovering said alkali metal salt of the oxidized product.

12. The process of claim 11 wherein said aryl alkyl ketone has the formula IV:

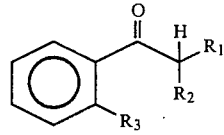  IV and wherein the oxidized product is a benzoic acid.

13. The process of claim 11 wherein an effective amount of activated charcoal is present.

14. The process of claim 11 wherein the liquid phase comprises an aprotic ether.

15. The process of claim 11 wherein the liquid phase comprises dimethoxyethane.

16. The process of claim 11 wherein the alkali metal hydroxide is sodium hydroxide.

17. The process of claim 11 wherein the aryl alkyl ketone has the formula V:

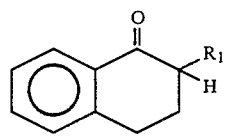

wherein $R_1$ is $C_1$–$C_{10}$ alkyl or $C_4$–$C_{10}$ cycloalkyl or aryl or hydrogen.

18. The process of claim 17 wherein $R_1$ is H and wherein the alkali metal salt of the oxidized product is acidified to produce the oxidized product having the formula:

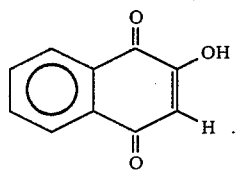

* * * * *